United States Patent
Bhagwatwar et al.

(10) Patent No.: US 12,194,047 B2
(45) Date of Patent: Jan. 14, 2025

(54) STABLE ANTIEMETIC EMULSIONS

(71) Applicant: STEPS BIOSCIENCES, INC., Newark, NJ (US)

(72) Inventors: Harshal Prabhakar Bhagwatwar, Hyderabad (IN); Manoj Nerurkar, Bangalore (IN)

(73) Assignee: STEPS BIOSCIENCES, INC., Newark, NJ (US)

( * ) Notice: Subject to any disclaimer, the term of this patent is extended or adjusted under 35 U.S.C. 154(b) by 79 days.

(21) Appl. No.: 17/531,216

(22) Filed: Nov. 19, 2021

(65) Prior Publication Data
US 2022/0160722 A1 May 26, 2022

(30) Foreign Application Priority Data
Nov. 20, 2020 (IN) .............................. 202041050531

(51) Int. Cl.
| | | |
|---|---|---|
| A61K 31/5377 | (2006.01) | |
| A61K 9/00 | (2006.01) | |
| A61K 9/107 | (2006.01) | |
| A61K 47/10 | (2017.01) | |
| A61K 47/12 | (2006.01) | |
| A61K 47/24 | (2006.01) | |
| A61K 47/44 | (2017.01) | |

(52) U.S. Cl.
CPC ........ *A61K 31/5377* (2013.01); *A61K 9/0019* (2013.01); *A61K 9/107* (2013.01); *A61K 47/10* (2013.01); *A61K 47/12* (2013.01); *A61K 47/24* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 9,561,229 B2 | 2/2017 | Ottoboni et al. | |
| 9,808,465 B2 * | 11/2017 | Ottoboni | ............... A61K 47/10 |
| 9,974,742 B2 | 5/2018 | Ottoboni et al. | |
| 9,974,793 B2 | 5/2018 | Ottoboni et al. | |
| 9,974,794 B2 | 5/2018 | Ottoboni et al. | |
| 10,500,208 B2 | 12/2019 | Ottoboni et al. | |
| 10,624,850 B2 | 4/2020 | Ottoboni et al. | |
| 10,953,018 B2 | 3/2021 | Ottoboni et al. | |
| 11,173,118 B2 | 11/2021 | Ottoboni et al. | |
| 2006/0188534 A1 | 8/2006 | Muller | |
| 2009/0209541 A1 | 8/2009 | Jain et al. | |
| 2016/0082013 A1 * | 3/2016 | Ottoboni | ............... A61K 9/0024 |

FOREIGN PATENT DOCUMENTS

| | | | |
|---|---|---|---|
| CN | 102379845 A | * | 3/2012 |
| EP | 2968575 B1 | | 6/2019 |

OTHER PUBLICATIONS

Zhang et al. "Mixed nanomicelles as potential carriers for systemic delivery of Z-DP-Dox, an FAPa-based doxorubicin prodrug: Formulation and pharmacokinetic evaluation". International Journal of Nanomedicine. 10: 1625-1636. (Year: 2015).*

Zhang et al. "Mixed nanomicelles as potential carriers for systemic delivery of Z-GP-Dox, an FAPa-based doxorubicin prodrug: formulation and pharmacokinetic evaluation". International Journal of Nanomedicine. 10: 1625-1636 (Year: 2015).*

Hippalgaonkar, Ketan, Soumyajit Majumdar, and Viral Kansara. "Injectable lipid emulsions advancements, opportunities and challenges." Aaps Pharmscitech11.4 (2010): 1526-1540.

* cited by examiner

*Primary Examiner* — Jeffrey S Lundgren
*Assistant Examiner* — Anthony Joseph Seitz
(74) *Attorney, Agent, or Firm* — Shumaker, Loop & Kendrick, LLP; Patrick B. Horne

(57) ABSTRACT

Emulsion formulations and systems for the intravenous or parenteral administration of neurokinin-1 (NK-1) receptor antagonists for treatment of emesis are provided. Methods for preparing the stable NK-1 receptor antagonist emulsions and pharmaceutical formulations are further provided. The emulsion formulations are prepared and characterized as a formulation and process that will allow an NK-1 receptor antagonist compound to be incorporated into an emulsion for intravenous injection and remain stable during the shelf life of the formulation. Specifically, emulsion formulations have an oil phase that includes oil, ethanol, egg lecithin, and the further addition of sodium oleate that is mixed with an aqueous phase and processed to form the emulsion formulation.

16 Claims, No Drawings

STABLE ANTIEMETIC EMULSIONS

The following specification describes the invention.

FIELD OF THE INVENTION

The disclosure relates generally to emulsion formulations and systems for the intravenous or parenteral administration of neurokinin-1 (NK-1) receptor antagonists for treatment of emesis. The emulsion formulations are stable for prolonged periods of time. Also described are methods for preparing the stable NK-1 receptor antagonist emulsions and pharmaceutical formulations.

BACKGROUND OF THE INVENTION

NK-I receptor is a tachykinin (NKA) substance P (SP) binding site, the vomiting center in the brainstem and the gastrointestinal tract. NK-I receptor antagonists such as aprepitant, rolapitant, netupitant or maropitant block the action of substance P by binding to the NK-I receptor (primarily in the central nervous system and periphery) and hence prevent vomiting. Future NK-1 antagonists under investigation include vofopitant, ezlopitant, CP 122721 (Pfizer), casopitant, netupitant, T2328, and vestipitant which are currently in various phases of investigation.

NK-1 receptor antagonists currently approved and marketed include aprepitant, netupitant, rolapitant HCl for human use, and maropitant for veterinary applications. Oral dosage forms may not be effective for patients suffering from emesis and may result in the delivery of incomplete and inaccurate dosages of the active compounds, and hence reduced efficacy. It is desirable to have injectable formulations to simplify treatment for these patients. Described herein are emulsions formulated for administering NK-1 antagonists to a patient by injection.

Liquid formulations containing NK-1 receptor antagonists having poor solubility can be very challenging to formulate for purposes of long-term storage and for administration. Aprepitant for example due to its poor aqueous solubility has been formulated as a prodrug in the form of fosaprepitant. Maropitant is available in the form of an inclusion complex with sulfo-butyl ether beta cyclodextrin. Another means of addressing this challenge is to prepare an emulsion which may allow preparation of an injectable formulation with a high drug loading.

Intravenous emulsions should have a very small droplet size to circulate in the bloodstream without causing capillary blockage and embolization, after formulation and through the shelf life of the emulsion. These size limits are typified by USP33-NF28 General Chapter <729> for Globule Size Distribution in Lipid Injectable Emulsions, which defines universal limits for (1) mean droplet size not exceeding 500 nm and (2) the population of large-diameter fat globules, expressed as the volume-weighted percentage of fat greater than 5 µm (PFAT5) not exceeding 0.05%, irrespective of the final lipid concentration.

All true emulsions are thermodynamically unstable and may over time undergo a range of transformations which tend to increase the droplet size. These include direct droplet coalescence, when two droplets collide and form a single new droplet; and aggregation, in which droplets adhere together to form larger masses. Aggregation may in some cases be a precursor of further coalescence into larger droplets and subsequent breakdown of the emulsion which is undesirable in pharmaceutical emulsions, specifically for parenteral administration.

Emulsion formulations must also be chemically stable. The drug substance, phospholipids or oils present in the emulsion may chemically degrade through oxidation, hydrolysis, and other mechanisms resulting in changes in the emulsion properties such as reduced potency, increased drug-related and non-drug related impurities, drop in pH, and such other changes. Any change in pH over the assigned shelf-life may be indicative of chemical degradation and is undesirable.

Instability can also be seen as formation of drug crystals in the emulsion composition on storage resulting in changes in droplet size as well as finally break down of the emulsion. Formation of crystals can also result in modified drug release properties. Presence of uncontrolled crystals in the emulsion compositions for parenteral administration not only poses a safety risk but also may result in compositions with varying pharmacokinetic characteristics.

Chinese patent application number CN102379845 describes emulsion compositions comprising aprepitant. The invention discloses an aprepitant microemulsion for injection. The aprepitant microemulsion consists of the following components in percentage by mass: 0.05 to 2 percent of aprepitant, 5 to 30 percent of oil for injection, 0.5 to 10 percent of emulsifier, 1 to 10 percent of co-emulsifier, 5 to 20 percent of protective agent and 60 to 80 percent of water for injection. The compositions have a pH in the range of 6.0-8.0 and the particle diameter is 50 nm-150 nm. The application is silent about the types of emulsifiers and buffers that could be useful in the inventive composition and process and ways to formulate a stable emulsion.

Beneficial emulsion formulations of aprepitant are commercially available in the United States from Heron Therapeutics under the brand name CINVANTI®. According to its label (Revised 10/2019), CINVANTI (aprepitant) injectable emulsion is a sterile, opaque, off-white to amber liquid in a single-dose vial for intravenous use. Each vial contains 130 mg aprepitant in 18 mL of emulsion. The emulsion also contains the following inactive ingredients: egg lecithin (2.6 g), ethanol (0.5 g), sodium oleate (0.1 g), soybean oil (1.7 g), sucrose (1 g), and water for injection (12 g). The emulsions are formulated to have final pH values in the range of 7.5-9.0 wherein the pH is adjusted using sodium oleate. The composition can be administered intravenously as an infusion or also as a bolus. According to the label, CINVANTI injectable emulsion vials must be refrigerated, store at 2° C.-8° C. (36° F.-46° F.), but can remain at room temperature up to 60 days. Prior to administration, the composition (18 ml per vial) is diluted with normal saline (0.9% sodium chloride injection, USP) or 5% dextrose for injection, USP.

A ready-to-use emulsion formulation of rolapitant for intravenous administration was approved in the US under the name VARUBI® but was subsequently withdrawn from the market due to severe hypersensitivity reactions attributed to the composition. The product contained large amounts of a solubilizer, stabilizer Kolliphor HS 15 in the composition, up to 4.0 g per vial of 92.5 ml product. Such nonionic surfactants as Polyethylene glycol (15)-hydroxystearate (Kolliphor HS $15^R$), Tween 80, Cremophor EL, etc. have been approved in injectable formulations but have been demonstrated to generate hypersensitivity reactions in clinical use.

The inventors have found surprisingly that beneficial oil in water emulsion compositions of NK-1 antagonists addressing some of the needs described above can be formulated by using combinations of higher concentrations of a phospholipid primary emulsifier (surfactant) in combination with varying concentrations of one or more co-emulsifiers (co-surfactants) or secondary emulsifiers such as sodium oleate, Kolliphor HS 15, Vitamin E TPGS, Transcutol, Polysorbates, Cremophors, etc.

In the present application, emulsion formulations were prepared and characterized to identify a formulation and process that will allow an NK-1 receptor antagonist compound to be incorporated into an emulsion for intravenous injection and remain stable during the shelf life of the formulation.

SUMMARY

The present disclosure sets forth injectable, pharmaceutically acceptable oil in water emulsions. Specifically, the present disclosure sets forth an oil phase for use in the injectable, pharmaceutically acceptable emulsion. The oil phase is mixed with an aqueous phase in the injectable, pharmaceutically acceptable emulsion. Processes for preparing the injectable, pharmaceutically acceptable emulsions are also disclosed. Further, processes for preparing the oil phase for mixing with an aqueous phase to form an injectable, pharmaceutically acceptable emulsion are further disclosed.

Embodiments of the present disclosure include an injectable pharmaceutically acceptable composition comprising an emulsion. The composition of the present disclosure may be stable for at least 12 months at refrigerated temperatures. The emulsion has an oil phase comprising aprepitant, an oil, a first emulsifier comprising a lecithin, a second emulsifier comprising sodium oleate, and ethanol. The emulsion also has an aqueous phase. The aqueous phase comprises a tonicity agent and water. The oil phase and the aqueous phase are mixed to form the emulsion.

Embodiments of the injectable pharmaceutically acceptable composition have a ratio of the first emulsifier to the second emulsifier, on a % w/w basis, may range from about 12% to about 30%, preferably from 12.93% to 29.68%. The pH of the emulsion may range from 6.0 to 9.0. The first emulsifier may comprise 16.5% to 25% w/w egg lecithin. In another embodiment, the first emulsifier may comprise 16.5% to 22.5% w/w egg lecithin. In each of the above embodiments, the second emulsifier may comprise 0.556% to 1.74% w/w sodium oleate. In one embodiment, the first emulsifier comprises 17.5% w/w egg lecithin and the second emulsifier comprises 0.60% sodium oleate.

In the embodiments of the present disclosure, the emulsion may have a zeta potential of −35 to −75 mV at a temperature of 2° C. The oil may be a soybean oil. Additionally, or alternatively, the oil may be selected from the group consisting of coconut oil, olive oil, soybean oil, safflower oil, corn oil, sesame oil, castor oil and cottonseed oil, triglycerides (long chain, medium chain and short chain triglycerides are all included within the scope of the term triglycerides), octyl and decyl glycerate, ethyl oleate, glyceryl linoleate, ethyl linoleate, glyceryl oleate, cholesteryl oleate/linoleate, or a mixture thereof.

In some embodiments, an injectable pharmaceutically acceptable composition comprises an emulsion having an oil phase comprising aprepitant; an oil; egg lecithin; sodium oleate; and absolute ethanol, that is further mixed with an aqueous phase comprising a tonicity agent and water. The oil phase may comprise 0.72% w/w aprepitant; 9.44% w/w soybean oil; 16.5% to 22.5% w/w egg lecithin; 0.566-1.74% w/w sodium oleate; and 2.78% w/w absolute ethanol. In one embodiment, the oil phase comprises 17.5% w/w egg lecithin and 0.60% w/w sodium oleate. The ratio of egg lecithin and sodium oleate to aprepitant may range from at least about 23.7 to about 33.6. The ratio of egg lecithin to sodium oleate, on a % w/w basis, may range from 12.93 to 29.68. The aqueous phase may comprise 5.56% w/w sucrose and water.

A process for preparing an injectable, pharmaceutically acceptable emulsion comprises:
(i) preparing an oil phase by (a) mixing aprepitant, an oil, ethanol, egg lecithin to form a clear solution (b) adding sodium oleate to oil phase of step (a) under mixing and optionally heating to form a uniform oil phase dispersion;
(ii) preparing an aqueous phase by mixing water, sucrose and optionally a buffer;
(iii) mixing the oil phase dispersion of step (i)(b) with the aqueous phase of step (ii) to form a coarse emulsion;
(iv) subjecting the coarse emulsion to size reduction using homogenization equipment to form a fine emulsion; and
(v) subjecting the fine emulsion of step iv to a sterile filtration process.

The oil phase in such a process may comprise 0.72% w/w aprepitant; 9.44% w/w soybean oil; 17.5% w/w egg lecithin; 0.60% w/w sodium oleate; and 2.78% w/w absolute ethanol and the aqueous phase may comprise a tonicity agent such as 5.56% w/w sucrose and water (q.s. to 100%).

A process for preparing an oil phase for mixing with an aqueous phase, to form an injectable, pharmaceutically acceptable emulsion, may be prepared by:
(i) mixing aprepitant, an oil, ethanol, egg lecithin to form a clear solution; and
(ii) adding sodium oleate to oil phase of step (a) under mixing and optionally heating to form a uniform oil phase dispersion.

Further embodiments include methods of using the presently disclosed aprepitant formulations to treat or prevent enmetic conditions by parenterally administering an effective amount of aprepitant disposed in such formulations either with or without further dilution.

The foregoing and other objects, features, and advantages of the embodiments will be apparent from the following more detailed descriptions of particular embodiments as further described below.

DETAILED DESCRIPTION

The following aspects and embodiments thereof described and illustrated below are meant to be exemplary and illustrative, not limiting in scope.

In one aspect, a pharmaceutical composition suitable for intravenous administration is provided which comprises a stable emulsion comprising an oil phase, wherein the oil phase comprises a NK-1 receptor antagonist, a surfactant and a co-surfactant; and an aqueous phase, wherein the aqueous phase comprises water, a tonicity agent, and a pH modifier. In certain embodiments the composition may also contain a preservative.

As used in this specification, the term "emulsion" or "emulsion formulation" means a colloidal dispersion of two immiscible liquids in the form of droplets, whose diameter, in general, is between 10 nanometers and 100 microns.

In some embodiments, the NK-1 receptor antagonist selected from the group comprising aprepitant, rolapitant, maropitant, and netupitant. In specific embodiments the NK-1 receptor antagonist is aprepitant.

In some embodiments, the composition is an oil-in-water emulsion comprising an oil wherein the oil is selected from the group consisting of coconut oil, olive oil, soybean oil, safflower oil, corn oil, sesame oil, castor oil and cottonseed oil, triglycerides (long chain, medium chain and short chain triglycerides are all included within the scope of the term triglycerides), octyl and decyl glycerate, ethyl oleate, glyceryl linoleate, ethyl linoleate, glyceryl oleate, cholesteryl oleate/linoleate, or a mixture thereof. In other embodiments, the oil is hydrolysed. In still other embodiments, the oil is structurally modified.

"Oil" refers to an organic liquid of mineral, vegetable, animal, essential, or synthetic origin, including, for example, aliphatic or wax-based hydrocarbons, aromatic hydrocarbons or mixed aliphatic, and aromatic hydrocarbons.

An "emulsifier" refers to a compound that deters the separation of the injectable emulsion into individual oil and aqueous phases. Emulsifiers useful in the present disclosure generally are non-toxic, stable and do not deteriorate in the preparation, compatible with the other ingredients of the stable emulsions of the present disclosure do not interfere with the stability or efficacy of the drugs contained in the emulsions. Preferred primary emulsifiers are phospholipids.

A "phospholipid" refers to a tri-ester of glycerol in which the secondary alcohol and one of the primary alcohols has been esterified with fatty acids and the other primary alcohol has been esterified with a phosphate group. Exemplary phospholipids useful in the present invention include, but are not limited to, phosphatidyl choline, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipid component of the drug delivery composition can be either a single phospholipid or a mixture of several phospholipids. The phospholipids should be acceptable for the chosen route of administration.

In some embodiments, the primary emulsifier comprises a phospholipid. In another embodiment, the emulsifier is selected from the group consisting of egg phospholipids, soy phospholipids, phosphatidylcholines, phosphatidylethanolamines, phosphatidylserines, phosphatidylglycerols, phosphatidylinositols, phosphatidic acids, mixed chain phospholipids, lysophospholipids, hydrogenated phospholipids, partially hydrogenated phospholipids, and mixtures thereof.

In one aspect, the phospholipids used as emulsifiers in the present invention are naturally occurring phospholipids from a natural origin. Soy lecithin and egg lecithin (including hydrogenated versions of these compounds) have been characterized in various compositions and are generally recognized to be safe, have combined emulsification and solubilization properties, and tend to be broken down into innocuous substances more rapidly than most synthetic surfactants.

The amount of phospholipids, by weight, in the emulsions of the present disclosure may be within a range of about 14% w/w to about 25% w/w or up to 30% w/w. In certain embodiments, the phospholipids in the emulsions are at a concentration, by weight, greater than 15% w/w, or greater than 18% w/w, or greater than 22% w/w.

Suitable co-emulsifiers include, but are not limited to, esters of polyethylene-glycol glycerol ethers, oil and wax based emulsifiers, glycerol monostearate, glycerine sorbitan fatty acid esters, propylene glycol mono- and di-fatty acid esters, polyoxyethylene sorbitan fatty acid esters, polyoxyethylene fatty acid esters, salts of fatty alcohol sulphates, sorbitan fatty acid esters, polyoxyethylene-polyoxypropylene co-polymers, and block co-polymers. In some embodiments the preferred co-emulsifier is sodium oleate.

The ratio of emulsifier to co-emulsifier can vary from a high concentration of primary emulsifier of 15-30% w/w of the composition and 0-10% of the co-emulsifier. The overall concentration of the emulsifier and co-emulsifier is envisaged to be greater than 15% up to 30% of the composition. Such high levels of these inert stabilizers are expected to provide NK-1 receptor antagonist containing emulsions of exceptional stability. An increase in viscosity, in combination with the use of high concentrations of lecithin, was evident in the embodiments of the present disclosure, as illustrated by the examples below.

Another embodiment of the invention describes the stabilization of the emulsion composition by defining the ratio of the primary emulsifier to the co-emulsifier. In particular, refer to Example 6, below, describing the titration of egg lecithin to sodium oleate to achieve zeta potential.

In some embodiments, the co-surfactant comprises a compound selected from ethanol, preferably absolute ethanol, benzyl alcohol, benzyl benzoate, Tweens, Kolliphor HS 15. Cremophors, vitamin E TPGS, Transcutol, and other such materials which have either solubilizing and/or emulsion stabilizing capabilities. These could be used either alone or in combination of more than one along with the primary emulsifier.

The term "buffer" or "buffered" as used herein means a solution containing both a weak acid and its conjugate base, whose pH changes only slightly upon addition of acid or base. Buffers for use according to the methods and compositions described herein include but are not limited to phosphate, citrate, Tris, carbonate, succinate, maleate, borate, MES, Bis-Tris, TEA, and other buffers known to persons skilled in the art.

In some embodiments, the pH modifier comprises a buffer. In other embodiments, the buffer is selected from the group consisting of phosphate buffer, citrate buffer, Tris buffer, carbonate buffer, succinate buffer, maleate buffer, and borate buffer. In still other embodiments, the buffer is selected from the group, phosphate buffered saline (PBS), and citrate buffer.

In an embodiment the invention is an injectable pharmaceutical emulsion comprising:

0.4 w/w % to 3.0 w/w % aprepitant (NK-1 receptor antagonist); greater than 15 w/w % egg yolk lecithin (primary emulsifier); 9 w/w % to 10 w/w % soybean oil; and 0-10% of a co-emulsifier, such as sodium oleate; and water wherein the pH of the emulsion ranges from 6.0 to 9.0.

In specific embodiments the egg yolk lecithin is at or above 16.5% w/w of the composition up to 25% or even 30% w/w of the emulsion composition. In further embodiments the pH of the emulsion may be adjusted to 6-7.5 using a reduced amount of sodium oleate or through the use of other buffers as described above.

In yet further embodiments the composition is free of ethanol. Some inventive compositions comprise preservatives such as benzyl alcohol, methyl or propyl parabens, etc. allowing multiple withdrawals from the same container. The emulsion preparations as described herein may further comprise a preservative in quantities that preserve the composition. Suitable preservatives used in some of the embodiments of present disclosure include, but are not limited to, disodium edetate, tocopherol, benzalkonium chloride, methyl, ethyl, propyl or butylparaben, benzyl alcohol, phenylethyl alcohol, benzethonium, chlorobutanol, potassium sorbate, or combination thereof.

In another aspect, a method for preparing an emulsion comprising an NK-1 receptor antagonist compound and suitable for parenteral administration is provided.

In some embodiments, the method comprises: i) preparing an oil phase by dissolving the active and emulsifier in ethanol, then adding in oil to generate an oil-based mixture; ii) preparing an aqueous phase by mixing water, optionally with other components such as buffer, pH modifier, osmotic/tonicity agent; iii) combining the oil and aqueous phases to form an emulsion under high speed homogenization and further subjecting the crude emulsion to high pressure homogenization to generate a microemulsion; and iv) sterilizing the pharmaceutical emulsion, wherein the final emulsion is suitable for injection into a subject.

In a specific embodiment, the pH modifier is added to the oil phase and the emulsion is then processed as per the earlier embodiment. In a further specific embodiment the pH modifier is sodium oleate. Accordingly, the process of making the emulsions of the present disclosure comprises: (i) preparing an oil phase by dissolving the active and emulsifier in ethanol, then adding in oil to generate an oil-based mixture; (ii) further adding sodium oleate to this oil phase, mixing with or optionally without heating the oil phase to disperse uniformly or dissolve the sodium oleate in the oil phase; (iii) preparing an aqueous phase by mixing water, optionally with other components such as buffer, osmotic/tonicity agent; (iv) combining the oil and aqueous phases to form an emulsion under high speed homogenization and further subjecting the crude emulsion to high pressure homogenization to generate a nanoemulsion; and (v) sterilizing the pharmaceutical emulsion, wherein the final emulsion is suitable for injection into a subject.

Another embodiment of the invention comprises defining the amount of sodium oleate or other pH modifier required for preparation of the stable emulsions with increasing amounts of egg lecithin. The inventors have surprisingly found that the amount of sodium oleate required to achieve the same zeta potential or pH as an emulsion with lower amounts of egg lecithin is not the same as when the egg lecithin concentration is increased. So, for example, an emulsion comprising 14% egg lecithin requires a very different amount of sodium oleate to achieve a particular zeta potential than an emulsion comprising 17.5% or 20% egg lecithin. The ability to balance the ratio of the egg lecithin to the sodium oleate with increasing concentrations of the egg lecithin is an inventive embodiment of the invention.

In some embodiments, the high-speed homogenization is performed for a period of time varying between 2 minutes to 60 minutes preferably from 10 minutes to 40 minutes, more preferably from 20 minutes to 30 minutes.

In some embodiments, the high-pressure homogenization is performed at a pressure of about 5000 psi (pounds per square inch) to 50,000 psi. In other embodiments, the high-pressure homogenization is performed at a pressure of about 20,000 to 25,000 psi.

In some embodiments, the sterilization of the emulsion may be done through a nylon filter with a pore size of about 0.2 µm (micrometres).

Oil Phase

The oil (hydrophobic) phase comprises of an oil. In specific embodiments, the oil is or comprises safflower oil, sesame oil, corn oil, olive oil, and/or soybean oil. In more specific embodiments, the oil is or comprises safflower oil and/or soybean oil. The oil is present in the emulsion at about 9% w/w, though this may vary between about 5% w/w to 12% w/w or 9% w/w to 10% w/w.

To generate the oil phase, the NK-1 receptor antagonist is first mixed with an emulsifier such as a phospholipid emulsifier.

The mixture of antagonist and emulsifier is dissolved in a co-surfactant such as a short chain alcohol (1 to 6 carbons). The mixture is mixed at an elevated temperature, such as at about 60° C. or 70° C. or at an elevated temperature within the range of about 50° C. or 70° C., until the NK-1 receptor antagonist and emulsifier are dissolved. This mixture is then combined with the oil, such as soybean oil, by mixing again at an elevated temperature such as at about 60° C. to produce the oil phase containing the NK-1 receptor antagonist. Excess co-surfactant can be removed by standard evaporation methods including heating, or pressure reduction, or a combination thereof such employed in a rotary evaporator.

Aqueous Phase

The aqueous phase of the NK-1 receptor antagonist emulsion can be a mixture of water and a tonicity agent, including those such as but not limited to sucrose, sorbitol, xylitol, glucose, trehalose, maltose, raffinose, lactose, mannitol, glycerin or dextrose, or a mixture thereof. Also included in the aqueous phase is a pH-modifying agent (pH modifier). The aqueous phase is produced by mixing water with the tonicity agent and pH modifier). Additional pH modifiers that may be used include but are not limited to sodium hydroxide, potassium hydroxide, magnesium hydroxide, Tris, sodium carbonate, and sodium linoleate. In some embodiments, the pH modifier comprises more than one pH modifier. The aqueous phase can readily form by mixing at room temperature.

The aqueous phase of the emulsion may further contain a buffering agent to promote stability of the emulsion formulation. The drug substance may degrade; for example, lipophilic drugs will partition into the oil phase, which will confer some degree of protection, but hydrolytic degradation may still occur at the oil-water interface. Possible chemical degradation within parenteral fat emulsions includes oxidation of unsaturated fatty acid residues present in triglyceride and lecithin, and hydrolysis of phospholipids leading to the formation of free fatty acids (FFA) and lysophospholipids. Such degradants lower pH, which may then promote further degradation. Thus, pH should be controlled during manufacture and emulsion formulations may include a buffering agent to provide additional control. Any decrease in pH over the assigned shelf-life may be indicative of chemical degradation. Suitable buffers are well known to the person skilled in the art and include, but are not limited to, a phosphate buffer, citrate buffer, Tris buffer, carbonate buffer, succinate buffer, maleate buffer, or borate buffer. In some embodiments a buffer such as Tris buffer can be used in addition to another pH modifier (e.g., oleate or sodium oleate) to adjust or modify the pH of the emulsion. In some embodiments, the buffer is selected from the group, phosphate buffered saline (PBS), and citrate buffer. In a particular embodiment, the aqueous phase comprises a buffer, that when mixed with the oil phase will provide a substantially isotonic oil in water emulsion.

Buffering agents useful for the presently described compositions include, but are not limited to, a phosphate buffer, citrate buffer, Tris buffer, carbonate buffer, succinate buffer, maleate buffer, or borate buffer. In a particular embodiment, the buffer is selected from the group, phosphate buffered saline (PBS), and citrate buffer. In a particular embodiment, the aqueous phase comprises a buffer, that when mixed with the oil phase will provide a substantially isotonic oil in water emulsion. In some embodiments, when the aqueous phase contains a buffering agent, the aqueous phase does not include a tonicity agent. Also, when a buffer is added to the aqueous phase, an additional pH-adjusting agent may not be added to the aqueous phase. It is understood that a buffer can be added to the aqueous phase or the buffer can be added to the emulsion.

In some embodiments, the aqueous phase of the emulsion contains a tonicity agent such as, for example, sucrose, sorbitol, xylitol, glucose, trehalose, maltose, raffinose, lactose, mannitol, glycerin or dextrose, or a mixture thereof. The tonicity agent is added to an aqueous phase having about 0% to 30%, 0% to 25% or about 20% of the tonicity agent (w/w). Accordingly, preferred embodiments include an emulsion in which the aqueous phase comprises a tonicity agent which imparts greater chemical and/or physical stability as compared to an emulsion wherein the aqueous phase contains less than about 10%, 15% or 20% w/w tonicity agent or more than about 30%, 40% or 50% w/w tonicity agent.

Pharmaceutical Emulsion Formulations

The pharmaceutical compositions comprising NK-1 receptor antagonists as disclosed herein are sterile oil-in-water emulsions comprising the aqueous and oil phases described above. Also encompassed by the disclosure are methods for preparing stable emulsions comprising the receptor antagonist which are suitable for intravenous administration and which can be prepared according to the conventional manufacturing procedures using aseptic techniques.

The aqueous phase is combined with the oil phase, under high-speed homogenization to produce a coarse emulsion. Examples provided are of NK-1 receptor antagonist emulsions which are produced using compositions and methods disclosed herein.

The pharmaceutical formulation may then be passed through a filter system at room temperature, and/or autoclaved, to achieve sterilization. The filters used to achieve sterilization may have a nominal pore size of 0.2 μm and may be of nylon, covalent charge filter).

In one embodiment, repeated homogenization cycles to achieve small oil globule/particle size may be necessary.

The composition of the present disclosure gives a product suitable for parenteral use because of low droplet size which can be diluted with an aqueous solution of sucrose, sorbitol, xylitol, glucose, trehalose, maltose, raffinose, lactose, maltose or dextrose 5% injection, or normal saline. The compositions of the disclosure are physico-chemically stable for at least 24 months at room temperature (25 degrees Celsius) without an increase in average droplet size or population of large-diameter fat globules above that allowed as stated in USP <729>.

The oil or particle droplet size, i.e. diameter, according to the present disclosure is measured using a dynamic light scattering (DLS) instrument, such as the Malvern Zetasizer 4000, Malvern Zetasizer Nano S90 or preferably the Malvern Zetasizer Nano ZS.

Medical Use

The pharmaceutical compositions of the present disclosure can be used for the prevention or treatment of emesis and provide a non-oral option for patients undergoing highly or moderately emetogenic chemotherapy such as chemotherapy used in cancer patients. The disclosure thus encompasses a method of treatment comprising intravenously administering an emulsion comprising a NK-1 receptor antagonist as described herein to a subject undergoing highly or moderately emetogenic chemotherapy whether the chemotherapy is an initial treatment or repeat courses of the chemotherapy. The pharmaceutical emulsions described herein can be used, for example, in preventing or treating acute and delayed nausea and vomiting associated with the chemotherapy or radiotherapy. The pharmaceutical compositions of the present disclosure can be administered either as an IV push or as an infusion after dilution with a diluent such as 0.9% Sodium Chloride Injection, USP or 5% Dextrose for Injection, USP. Exemplary uses of Aprepitant parenteral formulations include using Aprepitant to treat acute and delayed nausea and vomiting associated with initial and repeat courses of highly emetogenic cancer chemotherapy (HEC) including highdose cisplatin. Aprepitant also can be used to treat nausea and vomiting associated with initial and repeat courses of moderately emetogenic cancer (MEC) chemotherapy. The typical dosage for HEC (Single Dose Regimen)) in adults is 130 mg on Day 1 as an intravenous infusion over 30 minutes approximately 30 minutes prior to chemotherapy. The typical dosage for MEC (3-Day Regimen) in adults is 100 mg administered on Day 1 as an intravenous infusion over 30 minutes approximately 30 minutes prior to chemotherapy. Aprepitant can be part of a regimen that includes other medicaments such as a corticosteroid and a 5-HT3 antagonist. The Aprepitant formulations also may be useful for other antienemtic purposes such as preventing post operative nausea and vomiting (PONV). Thus, it is contemplated that the aprepitant formulations also could be administered on a prophylactic basis for preventing or moderating nausea and vomiting in patients undergoing medical treatments that are susceptible to causing nausea and vomiting in patients.

Examples: The following examples of TABLE 1 further describe the invention in greater detail and are not meant to be limiting in any way to the scope of the invention.

TABLE 1

Examples 1-5

| Sr. No. | Raw Material | Concentration, %w/w Example | | | | |
|---|---|---|---|---|---|---|
| | | 1 | 2 | 3 | 4 | 5 |
| 1. | Aprepitant | 0.72 | 0.72 | 0.72 | 0.72 | 0.72 |
| 2. | Egg lecithin | 14 | 16.5 | 14 | 14 | 14 |
| 3. | Absolute Ethanol | 2.78 | 2.78 | 2.78 | 2.78 | 2.78 |
| 4. | Sodium Oleate | 0.56 | 0.56 | 0.28 | 0.28 | — |
| 5. | Soybean oil | 9.44 | 9.44 | 9.44 | 9.44 | 9.44 |
| 6. | Sucrose | 5.56 | 5.56 | 5.56 | 5.56 | 5.56 |
| 7. | Kolliphor HS 15 | — | — | — | — | 0.56 |
| 8. | Water for injection QS | 100 | 100 | 100 | 100 | 100 |
| 9. | Sodium hydroxide | — | — | qs | qs | qs |
| pH | — | | 7.5-9.0 | 7.5-9.0 | 6.0-7.2 | 7.5-9.0 | 6.0-9.0 |

Step 1 Oil Phase Preparation 1.1 Combine weighed quantity of Egg lecithin (Lipoid E 80) and weighed quantity of Aprepitant together, add 150% of label claim of ethanol (41.7 mg/mL) to it, and close the lid. Heat to 55°-60° C. under stirring at 500 rpm for NLT 30 min or until clear solution is obtained.
1.2 Open the lid of the container, continue stirring and heating until 50% of the label claim of the ethanol is evaporated (i.e. until concentration of 105% of label claim of ethanol is achieved and also ensure clarity of solution is clear). Nitrogen purging or applying vacuum to be employed to remove the excess quantity of ethanol.
1.3 Add weighed quantity of Soybean oil to step 1.2 under stirring and mix for 15 min at 55-60° C.
In some examples Koiliphor HS 15 is added to this until a clear solution is obtained.
1.4 Cool the above solution to 2530° C.

2 Aqueous Phase Preparation 2.1 Collect 50% of batch size of Water for Injection (WFI) in suitable vessel and cool to 25 to 30° C.

Step 3 Sucrose and Sodium Oleate Solution Preparation 3.1 Collect 10% of batch size of Water for Injection (WFI) in suitable vessel and cool to 25 to 30° C.
3.2 Add weighed quantity of sucrose to step 3.1 under stirring at 500 rpm for NLT 15 min or until clear solution is obtained.
3.3 Heat the solution from step 3.2 to 30-35° C. Add weighed quantity of Sodium Oleate under stirring at 500 rpm for NLT 15 min or until clear solution is obtained and cool the solution to 25-30° C.

Step 4 Coarse Emulsion Preparation, Volume Makeup and High Shear Mixing 4.1 Add WFI from step no. 2.1 to step no. 1.4 under stirring at 1000 rpm and mix for NLT 15 min or until uniform off-white/amber color emulsion is observed.
4.2 Add the solution from step 3.3 to 4.1 under stirring at 1000 rpm and mix for NLT 15 min.
4.3 Make up the volume to the target batch size with \WI (25°-30° C.) and mix under high shear homogenizer (Ultra-Turrax® IKA 125) at 10,000 rpm for 60 minutes. Maintain the temperature during high shear homogenization between 20°-25° C.

Step 5 Fine Emulsion Preparation 5.1 Homogenize the coarse emulsion from step 4.3 using High Pressure homogenizer (GEA NIRO SOAVI PANDA plus 2000) at a pressure of 15,000-6,000 psig for 25 passes or until the particle size of D90 of <200 nm is achieved (Target: Mean Avg. Diameter NMT 99 nm). Maintain the temperature of the drug product during homogenization between 10-15° C.
5.2 Fill the emulsion in 20 mL clear vial with a fill volume of 18 mL, stopper under nitrogen, seal and store the vials at 2-8° C.

Example 6: Estimation of Sodium Oleate Quantity

Fine emulsions were prepared as described in Examples 1-5 above containing varying amounts of EL (16.5, 17.5, 20.5, 25% w/w). The emulsions were taken in 10 mL clear glass vial. Initial pH, GSD & zeta potential of emulsion was recorded. This emulsion was titrated with 5% sodium oleate solution to achieve target zeta potential of −35 to −75 mV at a temperature of 2-8° C. and a target pH of 7.5 to 9.0 with dropwise addition. The quantity required was noted. The final emulsion was evaluated for pH, GSD & zeta potential. Based on the data, sodium oleate quantity was estimated to achieve the target zeta potential with different EL composition. Data are described in TABLE 2 below.

Proposed Quantity of Sodium Oleate Required to Achieve Desired Zeta Potential

As egg lecithin concentration increases, the sodium oleate concentration also needs to be increased to achieve the desired zeta potential (Mv), which may range from −35 to −75 mV.

TABLE 2

| Batch Details | Average volume of 5% Sodium Oleate solution required for the sample eq. to 5 mL to achieve desired Zeta Potential | Additional Quantity of Sodium Oleate required (mg) | Additional Quantity of Sodium Oleate required (mg/mL) A | Sodium Oleate already available in formulation (mg/mL) B | Proposed Label claim of Sodium Oleate (mg/mL) (A + B) |
|---|---|---|---|---|---|
| 16.5% Egg Lecithin | 1 mL | 50 mg for 8 mL | 6.25 | 5.6 | 11.90 |
| 17.5% Egg Lecithin | 2.2 mL | 110 mg for 10 mL | 11.00 | 6.0 | 17.0 |
| 20% Egg Lecithin | 1.9 mL | 95 mg for 8 mL | 11.88 | 5.56 | 17.44 |
| 25% Egg Lecithin | 1.9 mL | 95 mg for 8 mL | 11.88 | 5.56 | 17.44 |

The compositions prepared as above, in TABLE 2, with egg lecithin concentrations of 16.5% to 25% w/w and the corresponding titrated amounts of sodium oleate were found to be chemically and physically stable for extended period of time at 25° C. The viscosity of the emulsion compositions increased with increasing concentrations of egg lecithin. The increased viscosity could be used to modify the release of aprepitant from the composition.

TABLE 3, below, compares the formulations of six exemplary formulations having egg lecithin levels ranging from 16.5% to 22.5% w/w and sodium oleate levels ranging from 0.556% to 1.74% w/w, which showed promising stability, and acceptable syringeability, processability and redispersibility when compared to the commercial Cinvanti (aprepitant) formulation.

TABLE 3

| | | Concentration, % w/w | | | | | | |
|---|---|---|---|---|---|---|---|---|
| | | | Sample | | | | | |
| | Raw Material | CINVANTI | 1 | 2 | 3 | 4 | 5 | 6 |
| 1 | Aprepitant | 0.72 | 0.72 | 0.72 | 0.72 | 0.72 | 0.72 | 0.72 |
| 2 | Egg Lecithin | 14.44 | 16.5 | 16.5 | 17.5 | 19.5 | 20.5 | 22.5 |
| 3 | Absolute Ethanol | 2.78 | 2.78 | 2.78 | 2.78 | 2.78 | 2.78 | 2.78 |
| 4 | Sodium Oleate | 0.556 | 0.566 | 0.556 | 0.60 | 0.67 | 0.93 | 1.74 |
| 5 | Soybean Oil | 9.44 | 9.44 | 9.44 | 9.44 | 9.44 | 9.44 | 9.44 |
| 6 | Sucrose | 5.56 | 5.56 | 5.56 | 5.56 | 5.56 | 5.56 | 5.56 |
| 8 | Water for Injection QS | 100 | 100 | 100 | 100 | 100 | 100 | 100 |
| pH | — | — | 7.5-9.0 | 7.5-9.0 | 7.5-9.0 | 7.5-9.0 | 7.5-9.0 | 7.5-9.0 | 7.5-9.0 |

Example 7: Scale-Up Batches

Three reproducible batches of the improved aprepitant injectable emulsion were prepared at a 5 liter scale to assess the processability, scalability and stability. The composition and detailed manufacturing process is provided below in TABLE 4 and TABLE 5, respectively. Results from this scale-up exercise with 16.5% w/w egg lecithin are further produced in TABLE 6.

TABLE 4

Composition:

| Product: Aprepitant Injectable Emulsion 130 mg/18 mL | | Study: Lab scale stability study | |
|---|---|---|---|
| Sr. | | | Composition |
| No. | Ingredients | Manufacturer | Qty mg/mL | Qty g/Batch |
| 1 | Aprepitant | Solara Active | 7.2 | 39.6* |
| 2 | Egg lecithin (LIPOIDE80) | Lipoid GmbH | 175 | 962.5 |
| 3 | Absolute Ethanol | Panreac Applichem ITW reagents | 27.78 | 168.19** |
| 4 | Sodium oleate | Lipoid GmbH | 5.7 | 31.35 |
| 5 | Soybean oil | Lipoid GmbH | 94.4 | 519.2 |
| 6 | Sucrose | Merck KGaA | 55.56 | 305.58 |
| 7 | Water for injection | In-house | Qs to 1 mL | Qs to 5500 mL |

*Quantity considering 100% potency.

**10% overages added to compensate for process losses.

TABLE 5

Brief Manufacturing Procedure:

| Phase | Ingredients | Order of addition | Observations |
|---|---|---|---|
| Oil Phase | Egg lecithin + Ethanol | Egg lecithin was solubilized in Ethanol by stirring at 40°-45° C. for 6 to 7 Hrs. Post to the solubilization this phase was kept at 2°-8 C. after purging the headspace with $N_2$ gas. | Clear, Dark Brown color viscous solution. |
| | Egg lecithin + Ethanol - Aprepitant | Next Day, the above phase was thawed to RT. Aprepitant was added and heated to 60°-65° C. for 4 Hrs. The solution was cooled to 35° C. on standing. | Clear, Dark Brown color viscous solution |
| | Egg lecithin + Ethanol + Aprepitant + Soybean oil | Weighed quantity of Soybean oil was added and mixed for 30 min. | Clear, Dark Brown color solution |
| | Egg lecithin + Ethanol + Aprepitant + Soybean oil + Sodium oleate | Weighed quantity of sodium oleate was added and mixed at RT for 2 Hrs. | Uniformly dispersed sodium oleate particles, Orange to brown color viscous dispersion |

TABLE 5-continued

Brief Manufacturing Procedure:

| Phase | Ingredients | Order of addition | Observations |
|---|---|---|---|
| Aqueous phase | WFI | 2.2 Kg of Water for Injection (N2 purged) was taken | Clear Solution |
| Preparation of Coarse Emulsion | Aq. phase + Oil phase | Aqueous phase was added to oil phase using peristaltic pump and mixed at 2000 rpm for 5 min at RT | Off white to pale yellow color emulsion with floating oil phase |
| Preparation of Stabilizer Solution | Water for Injection (550 g) + Sucrose | Weighed quantity of sucrose was added to Water for Injection (N2 purged) and mixed at RT for 30 min to completely dissolve. | Clear, colorless Solution |
| Volume make-up of coarse emulsion | Coarse Emulsion + Sucrose solution + Water for Injection | The stabilizer solution from above step was added using peristaltic pump to Coarse emulsion and mixed for 15 min. Volume was made to 5.492 Kg (Density of product: 0.9986 g/mL) using WFI This emulsion mixed at 8,000 rpm for 1 hour. The temperature was maintained between 20°-30° C. during the mixing. | Freely flowable, off White to pale yellow color emulsion |
| High Pressure Homogenization | Coarse Emulsion | The above coarse emulsion was homogenized using Microfluidizer homogenizer at a Pressure of 18,000 psi for 6 passes Temperature during homogenization was maintained between 10°-15° C. | Freely flowable, Pale Yellow to Amber color Emulsion |
| Filtration of Fine Emulsion | Fine Emulsion | The above fine emulsion was filtered through 0.45 + 0.2μ PES membrane filter (Sartopore 2, Cat# 5445307H9-OO) | Freely flowable, Pale yellow to Amber color emulsion |
| Filling, Stoppering and Sealing | Fine Emulsion | The filtered emulsion was filled in 20 mL USP type I vial (Siliconized), the headspace was purge with $N_2$ gas and stoppered with 20 mm coated rubber stopper. The vials were sealed with 20 mm red flip-off seals. Target Fill volume: 18.3 ± 0.3 mL | NA |
| Stability Study | Filled vials | The filled vials were loaded for stability study as per protocol no. STABP-DQA-FDL-0067 | NA |

TABLE 6

| | | | Stability Conditions | | | | | | | |
|---|---|---|---|---|---|---|---|---|---|---|
| | | | 5° ± 3° C. | | | | 25° C. ± 2° C./60% RH ± 5% RH | | | |
| Test Parameters | | Initial | 1 M_INV | 2 M_INV | 3 M_INV | 6 M_INV | 1 M_INV | 2 M_INV | 3 M_INV | 6 M_INV |
| Appearance | Opaque off white to amber emulsion | * | * | * | * | * | # | # | # | # |
| pH | | 8.34 | 8.01 | 8.06 | 7.98 | 8.01 | 7.70 | 7.58 | 8.00 | 7.55 |
| Osmolality (mOsm/Kg) | | 475 | 469 | 478 | 480 | 479 | 454 | 495 | 464 | 469 |
| Ethanol Content (%) | | 91.4 | 92.4 | 89.7 | 91.0 | | 93.3 | 91.6 | 90.9 | |
| Drug Partitioning | Aqueous phase (%) | 0.1 | 0.4 | 0.5 | 0.1 | 0.2 | 0.4 | 0.4 | 0.2 | 0.2 |
| | Oil Phase (%) | 95.6 | 97.8 | 97.9 | 97.6 | 99.6 | 96.7 | 96.7 | 97.2 | 100.0 |
| % Assay of Aprepitant | | 101.5 | 99.5 | 99.0 | 99.2 | 98.9 | 99.1 | 98.8 | 99.0 | 98.5 |
| Globule size Distribution | PDI | 0.252 | 0.284 | 0.283 | 0.277 | 0.271 | 0.203 | 0.197 | 0.182 | 0.163 |
| | Z-Average (nm) | 69.00 | 66.36 | 66.06 | 65.40 | 64.30 | 105.6 | 110.2 | 115.6 | 131.4 |
| | D10 nm | 40.1 | 35.3 | 32.3 | 39.0 | 35.1 | 70.0 | 70.8 | 79.0 | 88.0 |
| | D50 nm | 85 | 84.5 | 85.6 | 83.9 | 80.3 | 122 | 126 | 132 | 146 |

TABLE 6-continued

| | | Stability Conditions | | | | | | | |
|---|---|---|---|---|---|---|---|---|---|
| | | 5° ± 3° C. | | | | 25° C. ± 2° C./60% RH ± 5% RH | | | |
| Test Parameters | Initial | 1 M_INV | 2 M_INV | 3 M_INV | 6 M_INV | 1 M_INV | 2 M_INV | 3 M_INV | 6 M_INV |
| D90 nm | 154 | 162 | 160 | 154 | 156 | 215 | 225 | 220 | 244 |
| D99 nm | 220 | 244 | 239 | 219 | 234 | 311 | 327 | 313 | 338 |
| Zeta potential (mV) | −41.6 | −50.4 | −51.6 | −45.2 | −54.8 | −57.2 | −60.5 | −59.8 | −60.0 |
| Total impurities | BLOQ | BLOQ | BLOQ | BLOQ | BLOQ | BLOQ | BLOQ | BLOQ | BLOQ |
| In-vitro 5 min | 7 | NP | NP | 8 | NP | NP | NP | NP | NP |
| Drug 10 min | 59 | NP | NP | 58 | NP | NP | NP | NP | NP |
| Release 15 min | 80 | NP | NP | 70 | NP | NP | NP | NP | NP |
| (%) 20 min | 88 | NP | NP | 79 | NP | NP | NP | NP | NP |
| 30 min | 92 | NP | NP | 88 | NP | NP | NP | NP | NP |
| 60 min | 91 | NP | NP | 91 | NP | NP | NP | NP | NP |
| 90 min | 89 | NP | NP | 90 | NP | NP | NP | NP | NP |

\* Amber color, opaque emulsion;
\# Phase separation, white color layer at top surface and light amber color, opaque emulsion;
ND: Not Detected;
BLOQ: Below limit of quantification;
NA: Not Applicable;
NP: Not Performed;
NMT: Not more than;
NLT: Not less than
Note:
Any unknown impurities below LOQ levels are disregarded from the calculations and Known impurities even at BLOQ level (0.06%) are considered for calculation of total impurities.

As can be seen from Table 6, compositions embodying the present invention were stable for extended periods of time as seen from the data for pH, total impurities, ethanol content, acid value, drug partitioning, globule size distribution and zeta potential.

From the data it was also concluded that the proposed manufacturing process of formulation bulk is results in a stable and comparable product.

While this invention has been described with reference to embodiments or examples thereof, it shall be understood that such description is by way of illustration only and should not be construed as limiting the scope of the claimed embodiments. Accordingly, the scope and content of the embodiments or examples are to be defined only by the terms of the following claims. Furthermore, it is understood that the features of any embodiment or example discussed herein may be combined with one or more features of any one or more embodiments or examples otherwise discussed or contemplated herein unless otherwise stated.

The invention claimed is:

1. An injectable pharmaceutically acceptable composition comprising an emulsion having an oil phase comprising aprepitant, an oil, a first emulsifier comprising a lecithin, a second emulsifier comprising sodium oleate, and ethanol, mixed with an aqueous phase comprising a tonicity agent and water wherein the second emulsifier comprises 0.556% to 1.74% w/w sodium oleate and wherein the oil phase of the emulsion is prepared by
   (a) mixing the aprepitant, the oil, the ethanol, the lecithin to form a clear solution; and
   (b) adding the sodium oleate to the oil phase of step (a) under mixing and optionally heating to form a uniform oil phase dispersion.

2. The injectable composition of claim 1, wherein the pH of the emulsion ranges from 6.0 to 9.0.

3. The injectable composition of claim 1, wherein the first emulsifier comprises 16.5% to 25% w/w egg lecithin.

4. The injectable composition of claim 1, wherein the first emulsifier comprises 16.5% to 22.5% w/w egg lecithin.

5. The injectable composition of claim 4, wherein the first emulsifier comprises 17.5% w/w egg lecithin and the second emulsifier comprises 0.60% sodium oleate.

6. The injectable composition of claim 5, wherein the emulsion exhibits a zeta potential of −35 to −75 mV at a temperature of 2-8° C.

7. The injectable composition of claim 1, wherein the oil is soybean oil.

8. The injectable composition of claim 1, wherein the oil is selected from the group consisting of coconut oil, olive oil, soybean oil, safflower oil, corn oil, sesame oil, castor oil and cottonseed oil, triglycerides (long chain, medium chain and short chain triglycerides are all included within the scope of the term triglycerides), octyl and decyl glycerate, ethyl oleate, glyceryl linoleate, ethyl linoleate, glyceryl oleate, cholesteryl oleate/linoleate, or a mixture thereof.

9. The injectable composition of claim 1, wherein the composition is stable for at least 12 months at refrigerated temperatures.

10. An injectable pharmaceutically acceptable composition comprising an emulsion having an oil phase comprising: aprepitant; egg lecithin; sodium oleate; and absolute ethanol, mixed with an aqueous phase comprising: a tonicity agent and water wherein the oil phase comprises 0.566% to 1.74% w/w sodium oleate.

11. The injectable composition of claim 10, wherein the oil phase comprises: 0.72% w/w aprepitant; 9.44% w/w soybean oil; 16.5% to 22.5% w/w egg lecithin; and 2.78% w/w absolute ethanol.

12. The injectable composition of claim 11, wherein the tonicity agent comprises: 5.56% w/w sucrose.

13. The injectable composition of claim 12, wherein the oil phase comprises 17.5% w/w egg lecithin and 0.60% w/w sodium oleate.

14. A process for preparing an injectable, pharmaceutically acceptable emulsion comprising:
   (i) preparing an oil phase by (a) mixing aprepitant, an oil, ethanol, egg lecithin to form a clear solution (b) adding sodium oleate to the oil phase of step (a) under mixing and optionally heating to form a uniform oil phase dispersion;

(ii) preparing an aqueous phase by mixing water, sucrose and optionally a buffer;
(iii) mixing the oil phase dispersion of step (i) (b) with the aqueous phase of step (ii) to form a coarse emulsion;
(iv) subjecting the coarse emulsion to size reduction using homogenization equipment to form a fine emulsion; and
(v) subjecting the fine emulsion of step iv to a sterile filtration process;
wherein the sodium oleate comprises 0.556% to 1.74% w/w sodium oleate.

15. The process of claim 14 wherein the oil phase comprises: 0.72% w/w aprepitant; 9.44% w/w soybean oil; 16.5% to 25% w/w egg lecithin; 0.566-1.74% w/w sodium oleate; and 2.78% w/w absolute ethanol.

16. The process of claim 14, wherein the oil phase comprises: 0.72% w/w aprepitant; 9.44% w/w soybean oil; 17.5% w/w egg lecithin; 0.60% w/w sodium oleate; and 2.78% w/w absolute ethanol, and the aqueous phase comprises: 5.56% w/w sucrose and water (q.s. to 100%).

* * * * *